United States Patent [19]

Turková et al.

[11] 3,997,482

[45] Dec. 14, 1976

[54] HYDROPHILIC POLYMERIC CARRIERS OF BIOLOGICALLY ACTIVE COMPOUNDS AND METHOD OF PREPARING THE SAME

[75] Inventors: Jaroslava Turková, Cesky Brod; Jiři Čoupek, Prague, both of Czechoslovakia

[73] Assignee: Ceskoslovenska akademie ved, Prague, Czechoslovakia

[22] Filed: July 8, 1974

[21] Appl. No.: 486,350

[52] U.S. Cl. .................... 260/2.5 R; 260/17.4 SG; 424/78; 424/81; 526/16; 526/46; 526/328
[51] Int. Cl.² .......................................... C08F 8/18
[58] Field of Search ............... 260/2.5 R, 17.4 SG, 260/86.1 R, 89.5 R; 526/16, 46

[56] References Cited
UNITED STATES PATENTS

| | | | |
|---|---|---|---|
| 2,976,576 | 3/1961 | Wichterle et al. | 264/49 |
| 3,220,960 | 11/1965 | Wichterle | 260/2.5 |
| 3,520,949 | 7/1970 | Shepherd et al. | 260/857 |
| 3,663,467 | 5/1972 | Albright | 260/2.5 B |
| 3,778,393 | 12/1973 | Greber et al. | 260/17.4 SG |
| 3,867,329 | 2/1975 | Halpern et al. | 260/29.6 H |

OTHER PUBLICATIONS

Nature, vol. 214, pp. 1302–1304, 6/67.
Nature, vol. 215, pp. 1492–1492 9/67.

*Primary Examiner*—John Kight, III

[57] ABSTRACT

There is disclosed a carrier for biologically active compounds comprising a hydrophilic polymeric macroporous gel including a copolymer of a hydroxy alkyl ester of acrylic or methacrylic acid and a member selected from the group consisting of a cross-linking acrylate or methacrylate derived from the corresponding acid and a bi- or trifunctional alcohol and bismethacrylamide, bisacrylamide and divinylbenzene, the hydroxy alkyl ester further containing the reaction product thereof with BrCN.

17 Claims, No Drawings

HYDROPHILIC POLYMERIC CARRIERS OF BIOLOGICALLY ACTIVE COMPOUNDS AND METHOD OF PREPARING THE SAME

This invention relates to new dry hydrophilic polymeric carriers for biologically active compounds and methods for their preparation. The invention relates more particularly to carriers which are suitable for immobilization of compounds containing one or more primary amine groups in the molecule.

The art indicates that reaction with cyanogen bromide is one of the more popular methods for activation of common carriers of biologically active compounds, such as those used in affinity chromatography or as catalysts. This latter method has been worked out by Axen et al. Another method (Nature 214, 1302/1967; ibid.215, 1491 (1967)) finds application, especially with polysaccharide carriers. According to this method, cyanogen bromide is allowed to react with an agarose gel in an alkaline medium. After the reaction is completed, the suspension of the activated gel is rapidly washed and immediately mixed with a solution of the biologically active compound (affinant). It is taught by the reference that washing and mixing with the affinant ought not to last longer than 90 seconds. This latter requirement places a rather onerous burden upon the expertise and technical skill of the worker who is required to perform the reaction.

It has also been found that the introduction into the production of a dry activated agarose gel removes some but not all of the complications connected with the necessity to activate the gel immediately before binding the affinant and additionally makes the process that much more convenient.

Substantial disadvantages of polysaccharide carriers in affinity chromatography, namely, the low mechanical and hydrolytic stability, easy contamination by the microorganisms, unsuitable porosity for some applications non-specific sorption occuring in some cases and lastly, the relatively high price, can be substantially overcome by this invention.

It is accordingly an object of the invention to avoid one or more drawbacks of the prior art.

It is another object of the invention to provide for new and novel carriers for biologically active materials and methods of preparing same.

These and other objects and advantages of the invention will become more apparent from the detailed description and the claims which follow hereinafter.

Broadly speaking the invention includes the provisions of a carrier for biologically active compounds comprising a hydrophilic polymeric macroporous gel including a copolymer of a hydroxy alkyl ester of acrylic or methacrylic acid and a member selected from the group consisting of a cross-linking acrylate or methacrylate derived from the corresponding acid and a bi- or trifunctional alcohol and bismethacrylamide, bisacrylamide and divinylbenzene, said hydroxy alkyl ester further containing the reaction product thereof with BrCN, a method for making same and uses therefor.

It is to be noted, that the invention therefore contemplates new hydrophilic polymeric carriers for biologically active compounds comprising a substantially dry hydrophilic polymeric macroporous gel containing hydroxyl groups partly substituted by the reaction of the former with BrCN. By the foregoing there is meant a carrier which includes a copolymer of the hydroxy esters of methacrylic or acrylic acid with at least one cross-linking acrylate or methacrylate of a bifunctional or trifunctional alcohol, which cross-linking materials contain two or more acrylic or methacrylic groups in their molecule, or with bisacrylamides, bismethacrylamides or divinylbenzene.

The copolymer will generally comprise about 10 to 90% of said ester, preferably about 10 to 90%, with about 10 to 90% by weight of said cross-linking member. Suitable hydroxy esters of the aforementioned group include hydroxyethyl acrylate, hydroxyethyl methacrylate, hydroxypropyl acrylate and methacrylate, diethylenglycol methacrylate and N-hydroxypropyl methacrylamide. The cross-linking acrylate or methacrylate referred to above include ethylenediacrylate, ethylenedimethacrylate, diethyleneglycoldimethacrylate, diethyleneglycoldiacrylate and oligoethyleneglycol dimethacrylate. Suitable alcohols from which the latter may be derived include ethyleglycol, diethyleneglycol, oligo and polyethyleneglycol.

The copolymers can be made by processes known in the art for making such materials and need not be further detailed herein.

The method of preparation of the gel material itself is by the activation of the gel with about 5 to 50%, preferably 30 to 90% cyanogen bromide. Generally an aqueous solution is employed containing 3 to 25% BrCN, preferably 10 to 15%.

The activation of the gel can be carried out in aqueous solution, such as water solution; the gel activated in this way is freed from water by dehydration with an organic solvent, such as, ethylalcohol aqueous, ethylalcohol absolute, acetone and dioxane. The amount of solvent employed is substantially non-critical and may vary from about 200 to 500% by weight, based upon the weight of the combined weight of the gel-water mixture. The gel is preferably dried after its activation with cyanogen bromide by removing the water by vacuum distillation at a temperature under its freezing point, i.e., by freeze drying.

It is preferable to add 5 to 15%, preferably 10 to 12% polysaccharide and/or monosaccharide to stabilize the gel activated by cyanogen bromide during freeze drying, e.g., dextrane and lactose, as suitable mixtures. The foregoing are preferably both added, the order of addition being substantially non-critical.

It has been found by a comparison of the mechanical stabilities of a homogeneous and a macroporous gel in contact with a solvent, that there exists a preference for the macroporous materials which have a rigid inner structure. This property becomes extremely important particularly in the technological application of larger amounts of the material in larger sized equipment. The chemical stability of the activated material can be substantially enhanced by methods known in the art by immobilization of the reactive groups on the solid surface. Therefore, it is not surprising that a macroporous gel activated with cyanogen bromide remains active after a long period of time, even without the application of stabilizing additives which are necessary in the activation and storage of homogeneous materials. Elution of the stabilizer, before binding of the affinant, which is necessary with the homogeneous gels of the prior art need not be carried out herein. If an especially high storage stability is required, almost total suppression of the deactivating reaction can be achieved by stabilization of the macroporous active gel.

The costs involved for the drying operation also play an important role in the production of the dry active gel for immobilization of the affinant. Even here, the non-swelling rigid polymeric beam texture of the macroporous gel is evidently easier to dry when compared with the heavily swollen homogeneous material of the prior art, concerning both drying time and the amount of removed water. In the prior art, very delicate technology and a low operating temperature have to be used for the drying, because of the low thermal stability of the active functional groups on the gel. Therein, rather costly drying methods need to be used, e.g. lyophilization or dehydration with solvents.

The gel used for activation has to possess, besides the macroporous structure, a sufficient amount of free hydroxyl groups operative to react with cyanogen bromide. Therefore, the gels used were prepared according to Czechoslovak Patent No. 150,819 based on Application No. PV 7919-70 corresponding to U.S. Ser. No. 281,288 and British Pat. No. 1,370,477, by suspension copolymerization of hydroxy alkyl esters, oligo- or polyglycol esters of acrylic or methacrylic acid with cross-linking comonomers containing two or more acrylic or methacrylic residues in their molecule or with divinylbenzene. The disclosure of the aforementioned application is incorporated herein by reference.

The biological activity of the compounds thus prepared by binding the affinant can be determined in the usual manner known in the art.

The following Examples are offered by way of illustration only and are not to be considered as limiting the scope of the invention. All parts, proportions and ratios therein, as well as in the appended claims are by weight unless indicated otherwise.

EXAMPLE 1

A hydrophilic macroporous gel (5 parts by wt.), prepared by precipitation suspension copolymerization of 2-hydroxyethyl methacrylate with ethylene dimethacrylate (3:2) in the presence of a solvent system consisting of cyclohexanol and dodecylalcohol (9:1) and having a molecular weight exclusion limit of 300,000 (Spheron 300), is swollen in distilled water to equilibrium. The swollen gel is stirred into an equal volume of distilled water; a vessel with the suspension is placed on a magnetic stirring table and a glass electrode is immersed into the suspension. An aqueous solution of cyanogen bromide (20 wt. parts of a 10% solution) is added to the suspension; fresh cyanogen bromide solution is always prepared several minutes before the reaction has been carried out. The suspension is adjusted to a pH of 11 with a 4N NaOH solution immediately after the addition of cyanogen bromide and this pH is maintained by a dropwise addition of 4N NaOH for 12 minutes at continuous stirring or until the washing step. The suspension is then washed on a sintered-glass filter with a twenty-fold volume of cool 0.1M sodium hydrogen carbonate (pH 9), based on the original volume of the swollen gel. The washing does not take longer than two minutes. After washing and removal of the liquid, the activated gel is divided into two portions — fraction A and fraction B.

A. The first half — fraction A, is immediately stirred into 10 ml of 0.1 N solution of sodium hydrogen carbonate (pH 9) and 1 g of chymotrypsin. The suspension is stirred on a magnetic stirring table at 4° C for 24 hours. After completion of the reaction, the gel is gradually washed with the following buffer solutions: 0.1 M sodium borate and 1M NaCl (pH 8.5); 0.1M sodium acetate and 1M NaCl (pH 4.1); 0.01M sodium acetate (pH 4.1). If more than 10 ml of the gel has been activated, the washing is carried out in a column of the corresponding size; the flow rate is adjusted to 8 ml/hr. Washing with the first buffer solution takes 48 hours and with the further two solutions, 24 hours each. If less than 10 ml of the swollen gel is activated, the washing is carried out on a sintered-glass filter; the volume of the first buffer solution corresponds to the forty-fold volume of the swollen gel, the volume of the further two buffer solutions to its thirty-fold volume. The gel prepared in this way is used for affinity chromatography and its proteolytic and esterase activities are analytically determined. The capacity is 12.2 mg of chymotrypsin per ml of the swollen gel.

B. The second half of the gel activated with cyanogen bromide — fraction B, is stirred at ambient temperature into water - alcohol mixtures with gradually increasing alcohol concentration (50%, 60%, 70%, 80% and 90%), the preceding aqueous alcohol is always separated from the gel by centrifugation. In the last step of dehydration, the gel is stirred into absolute ethanol, centrifuged and dried in a vacuum desiccator at a laboratory temperature (ambient — the drying takes about 24 hours). The activity of the gel dried in this way amounts to 70% of the fraction A activity. After 6 weeks of storage at this temperature (4° C), chymotrypsin is linked to the gel, which is previously swollen in 0.1N NaHCO$_3$ solution by the procedure described in the paragraph A. The gel capacity is 6.6 mg of chymotrypsin per 1 ml of the swollen gel. Proteolytic activity expressed in A$_{280}$ per mg of linked chymotrypsin is 0.038 units/min.mg and is the same in both fractions.

EXAMPLE 2

The hydrolytic macroporous gel is activated by the same procedure as in Example 1. After washing and removal, the gel is mixed with a solution of 5 wt. parts of dextrane having a molecular weight of 40,000 and 5 wt. parts of lactose in 100 wt. parts of water, centrifuged and lyophilized (freeze drying). The dry lyophilized gel has a capacity for reaction with chymotrypsin, 11.8 mg/ml CHT. The reaction of the activated gel with chymotrypsin, described in Example 1, is preceded by washing with 50 wt. parts of 0.1M NaHCO$_3$ solution.

Although this invention has been described with reference to certain specific Examples, it will be apparent to those skilled in the art that various modifications may be made thereto which fall within its scope.

We claim:

1. A dry hydrophilic polymeric carrier for biologically active compounds comprising the reaction product of 5 to 50% by weight of BrCN and a macroporous gel copolymer of (1) a hydroxy alkyl ester of acrylic or methacrylic acid and (2) about 10 to 90% by weight of a member selected from the group consisting of (a) a cross-linking acrylate or methacrylate derived from the corresponding acid and a bi - or trifunctional alcohol and (b) bismethacrylamide, bisacrylamide and divinylbenzene, said hydroxy alkylester (1) further containing a sufficient amount of free hydroxyl groups operative to react with said BrCN.

2. A carrier as defined in claim 1 wherein component (a) contains at least two acrylic or methacrylic moieties per molecule.

3. A carrier as defined in claim 1 wherein hydroxy alkyl ester (1) is 2-hydroxy ethyl methacrylate and said cross-linking material (2) is ethylene dimethacrylate.

4. A carrier as defined in claim 1 wherein said copolymer is prepared by suspension polymerization.

5. A method of preparing the carrier as defined in claim 1 comprising activating a macroporous gel copolymer of (1) a hydroxy alkyl ester of acrylic or methacrylic acid and (2) about 10 to 90% by weight of a member selected from the group consisting of (a) a cross-linking acrylate or methacrylate derived from the corresponding acid and a bi- or trifunctional alcohol and (b) bismethacrylamide, bisacrylamide and divinylbenzene said hydroxy alkylester (1) further containing free hydroxyl groups with 5 to 50% by weight of BrCN.

6. A method as defined in claim 5 wherein approximately 5 to 50% by weight of BrCN is employed.

7. A method as defined in claim 5 wherein said step of activating said gel is carried out in an aqueous media.

8. A method as defined in claim 7 wherein said media is water.

9. A method as defined in claim 7 wherein the gel thus activated is dehydrated by means of an organic solvent.

10. A method as defined in claim 5 wherein said gel is dried subsequent to said step of activation.

11. A method as defined in claim 10 wherein said drying is carried out by vacuum distillation.

12. A method as defined in claim 10 wherein at least one of a poly or monosaccharide is added to said gel prior to said step of drying.

13. A method as defined in claim 12 wherein said unit (3) is selected from the group consisting of dextran, lactose and suitable mixtures thereof.

14. A method as defined in claim 5 wherein said BrCN is employed as a 3 to 25% aqueous solution.

15. A method as defined in claim 5 wherein the pH of said activated gel is adjusted to about 11.

16. A method as defined in claim 15 wherein said adjusted pH is maintained until such activation is carried out.

17. A method as defined in claim 16 wherein said activated gel subsequent to pH adjustment is washed with sodium hydrogen carbonate.

* * * * *